(12) United States Patent
Dougal (10) Patent No.: US 9,079,021 B2
(45) Date of Patent: Jul. 14, 2015

(54) ELECTROMAGNETIC RADIATION AND ITS THERAPEUTIC EFFECT

(75) Inventor: Gordon Dougal, Durham (GB)

(73) Assignee: Virulite Distribution Limited, Spennymoor, Durham (GB)

( * ) Notice: Subject to any disclaimer, the term of this patent is extended or adjusted under 35 U.S.C. 154(b) by 164 days.

(21) Appl. No.: 13/003,958

(22) PCT Filed: Jul. 14, 2009

(86) PCT No.: PCT/GB2009/050848
§ 371 (c)(1), (2), (4) Date: Mar. 4, 2011

(87) PCT Pub. No.: WO2010/007419
PCT Pub. Date: Jan. 21, 2010

(65) Prior Publication Data
US 2011/0178582 A1    Jul. 21, 2011

(30) Foreign Application Priority Data
Jul. 14, 2008    (GB) .................................. 0812753.2

(51) Int. Cl.
*A61N 5/06*    (2006.01)

(52) U.S. Cl.
CPC ............. *A61N 5/0613* (2013.01); *A61N 5/0601* (2013.01); *A61N 5/062* (2013.01); *A61N 2005/0636* (2013.01); *A61N 2005/0645* (2013.01); *A61N 2005/0652* (2013.01); *A61N 2005/0659* (2013.01)

(58) Field of Classification Search
CPC ........... A61N 5/062; A61N 2005/0652; A61N 5/0601

USPC .................................. 606/88, 89; 607/88, 89
See application file for complete search history.

(56) References Cited

U.S. PATENT DOCUMENTS

| | | |
|---|---|---|
| 3,473,868 A | 10/1969 | Newman et al. |
| 3,533,683 A | 10/1970 | Stark et al. |
| 4,641,349 A | 2/1987 | Flom et al. |
| 4,878,891 A | 11/1989 | Judy et al. |
| 4,917,084 A | 4/1990 | Sinofsky |
| 4,930,504 A | 6/1990 | Diamantopoulos et al. |

(Continued)

FOREIGN PATENT DOCUMENTS

| | | |
|---|---|---|
| DE | 40 03 477 | 8/1991 |
| DE | 298 20 468 | 5/2000 |

(Continued)

OTHER PUBLICATIONS

Combined Search and Examination Report for United Kingdom Application No. GB0912206.0 mailed on Nov. 10, 2009.

(Continued)

*Primary Examiner* — Lynsey Crandall
*Assistant Examiner* — Sebastian X Lukjan
(74) *Attorney, Agent, or Firm* — Myers Bigel Sibley & Sajovec, PA (57) ABSTRACT

An electromagnetic radiation therapy system comprising an apparatus that emits electromagnetic radiation centred at or around 1072 nm and configured so as to be placed around a large proportion or the whole of a human or animal body. The invention also includes methods of treating diseases associated with a lack of compliance and or elasticity of vessels such as airway and/or blood vessels.

11 Claims, 5 Drawing Sheets

(56) References Cited

U.S. PATENT DOCUMENTS

| | | | |
|---|---|---|---|
| 4,951,663 | A | 8/1990 | L'Esperance, Jr. |
| 5,066,291 | A | 11/1991 | Stewart |
| 5,259,380 | A | 11/1993 | Mendes et al. |
| 5,348,551 | A | 9/1994 | Spears et al. |
| 5,445,146 | A | 8/1995 | Bellinger |
| 5,464,436 | A | 11/1995 | Smith |
| 5,478,239 | A | 12/1995 | Fuerst et al. |
| 5,500,009 | A | 3/1996 | Mendes et al. |
| 5,507,716 | A | 4/1996 | LaBerge et al. |
| 5,527,350 | A | 6/1996 | Grove et al. |
| 5,630,811 | A | 5/1997 | Miller |
| 5,658,323 | A | 8/1997 | Miller |
| 5,707,403 | A | 1/1998 | Grove et al. |
| 5,743,901 | A | 4/1998 | Grove et al. |
| 5,784,145 | A | 7/1998 | Ghodse et al. |
| 5,805,267 | A | 9/1998 | Goldman |
| 5,818,048 | A | 10/1998 | Sodickson et al. |
| 5,849,035 | A | 12/1998 | Pathak et al. |
| 5,868,731 | A | 2/1999 | Budnik et al. |
| 5,913,883 | A | 6/1999 | Alexander et al. |
| 5,989,245 | A | 11/1999 | Prescott |
| 6,027,495 | A | 2/2000 | Miller |
| 6,063,108 | A | 5/2000 | Salansky et al. |
| 6,091,546 | A | 7/2000 | Spitzer |
| 6,113,237 | A | 9/2000 | Ober et al. |
| 6,149,272 | A | 11/2000 | Bergner et al. |
| 6,179,830 | B1 | 1/2001 | Kokubu |
| 6,193,373 | B1 | 2/2001 | Apple et al. |
| 6,334,683 | B2 | 1/2002 | Apple et al. |
| 6,358,272 | B1 | 3/2002 | Wilden |
| 6,471,716 | B1 | 10/2002 | Pecukonis |
| 6,887,260 | B1 | 5/2005 | McDaniel |
| 6,986,765 | B2 | 1/2006 | Sumiya et al. |
| 7,060,061 | B2 | 6/2006 | Altshuler et al. |
| 7,549,984 | B2 * | 6/2009 | Mathis ............. 604/509 |
| 7,730,893 | B2 | 6/2010 | Dougal |
| 2001/0028309 | A1 | 10/2001 | Torch |
| 2003/0058492 | A1 | 3/2003 | Wakiyama |
| 2004/0093043 | A1 | 5/2004 | Edel et al. |
| 2004/0122491 | A1 | 6/2004 | Strong |
| 2004/0225340 | A1 | 11/2004 | Evans |
| 2005/0024853 | A1 | 2/2005 | Thomas-Benedict |
| 2005/0187579 | A1 * | 8/2005 | Danek et al. ............. 607/1 |
| 2005/0234383 | A1 | 10/2005 | Dougal |
| 2006/0271131 | A1 | 11/2006 | Passy et al. |
| 2007/0123958 | A1 * | 5/2007 | Laufer ............. 607/93 |
| 2007/0129778 | A1 * | 6/2007 | Dougal ............. 607/88 |
| 2010/0222647 | A1 * | 9/2010 | Hashimshony et al. ...... 600/301 |

FOREIGN PATENT DOCUMENTS

| | | |
|---|---|---|
| DE | 100 49 068 | 9/2001 |
| DE | 102 01 904 | 7/2003 |
| DE | 102 37 620 | 3/2004 |
| EP | 0533585 A1 | 3/1993 |
| EP | 0695559 A2 | 2/1996 |
| GB | 2360461 A | 9/2001 |
| GB | 2415387 A | 12/2005 |
| WO | WO 97/47993 A1 | 12/1997 |
| WO | WO 98/23329 A1 | 6/1998 |
| WO | WO 99/19024 A | 4/1999 |
| WO | WO 99/19024 A1 | 4/1999 |
| WO | WO 01/30292 A2 | 5/2001 |
| WO | WO 2004/000150 A1 | 12/2003 |
| WO | WO 2006/028465 A1 | 3/2006 |
| WO | WO 2006/030403 | 3/2006 |
| WO | WO 2006/108093 A2 | 10/2006 |
| WO | WO 2006/108093 A3 | 10/2006 |
| WO | WO 2009/038720 A2 | 3/2009 |

OTHER PUBLICATIONS

Abergel et al. "Laser Treatment of Keloids: A Clinical Trial and an in Vitro Study with Nd:YAG Laser" *Lasers in Surgery and Medicine* 4:291-295 (1984).

Abergel et al. "Nonthermal Effects on Nd:YAG Laser on Biological Functions of Human Skin Fibroblasts in Culture" *Lasers in Surgery and Medicine* 3:279-284 (1984).

Agaiby et al. "Laser modulation of angiogenic factor production by T-lymphocytes" *Lasers in Surgery and Medicine* 26:357-363 (2000).

Almeida-Lopes et al. "Comparison of the Low Level Laser Therapy Effects on Cultured Human Gingival Fibroblasts Proliferation Using Different Irradiance and Same Fluence" *Lasers in Surgery and Medicine* 29:179-184 (2001).

Castro et al. "Effects of the Nd:YAG Laser on DNA Synthesis and Collagen Production in Human Skin Fibroblast Cultures" *Annals of Plastic Surgery* 11(3):214-222 (1983).

Dougal et al. "A pilot study of treatment of herpes labialis with 1072 nm narrow waveband light" *Clinical and Experimental Dermatology* 25:149-154 (2001).

International Search Report for PCT/GB2005/002433; date of mailing Aug. 18, 2005.

Kreisler et al. "Low Level 809-nm Diode Laser Induced in Vitro Stimulation of the Proliferation of Human Gingival Fibroblasts" *Lasers in Surgery and Medicine* 30:365-369 (2002).

Loevschall et al. "Effect of Low Level Diode Laser Irradiation of Human Oral Mucosa Fibroblasts in Vitro" *Lasers in Surgery and Medicine* 14:347-354 (1994).

Mohanty et al. Comet Assay Measurements of DNA Damage in Cells by Laser Microibeams and Trapping Beams with Wavelengths Spanning a Range of 308 NM to 1064 NM *Radiation Research* 157(4):378-385 (2002).

Mokhtar et al. "Double-Blind, Placebo-Controlled Investigation of the Effect of Combined Phototherapy/Low Intensity Laser Therapy Upon Experimental Ischaemic Pain in Humans" *Lasers in Surgery and Medicine* 17:74-81 (1995).

Pereira et al. "Effect of Low-Power Laser Irradiation on Cell Growth and Procollagen Synthesis of Cultured Fibroblasts" *Lasers in Surgery and Medicine* 31:263-267 (2002).

Sakihama, Hideki "Effect of a Helium-Neon Laser on Cutaneous Inflammation" *The Kurame Medical Journal* 42:299-305 (1995).

Vecchio et al. "A Double-Blind Study of the Effectiveness of Low Level Laser Treatment of Rotator Cuff Tendinitis" *British Journal of Rheumatology* 32:740-742 (1993).

Spicer et al.; Lasers in Dermatology, Journal of the American Academy of Dermatology, Jan. 1996.

Steller et al.; Lasers in Surgery, Laser Applications in Medicine and Biology, vol. 2., 1974 pp. 246-249.

Notification of Transmittal of the International Search Report and the Written Opinion of the International Searching Authority, or the Declaration corresponding to International Application No. PCT/GB2006/002153 mailed Nov. 10, 2006.

International Preliminary Report on Patentability and Written Opinion dated Jan. 27, 2011 for PCT/GB2009/050848.

Davis, Christopher C., *Laser & Electro-Optics*, Cambridge University Press, p. 289 (1996).

International Preliminary Report on Patentability and Written Opinion of the International Searching Authority for International Application No. PCT/EP2010/054762; Date of Mailing: Oct. 27, 2011; 16 pages.

International Search Report and Written Opinion of the International Searching Authority for International Application No. PCT/EP2010/054762; Date of Mailing: Jun. 28, 2010; 16 pages.

* cited by examiner

ELECTROMAGNETIC RADIATION AND ITS THERAPEUTIC EFFECT

RELATED APPLICATIONS

The present application is a 35 U.S.C. §371 national phase application of PCT International Application No. PCT/GB2009/050848 having an international filing date of Jul. 14, 2009, claiming priority to Great Britain Patent Application No. 0812753.2, filed Jul. 14, 2008. The disclosures of each application are incorporated herein by reference in their entireties. The above PCT International Application was published in the English language as International Publication No. WO 2010/007419 A1.

The present invention relates to an electromagnetic radiation therapy system comprising an apparatus that emits electromagnetic radiation centred at or around particular therapeutic frequencies that is configures so as to be placed around at least a part of a body and for treating large areas of the body. The invention also includes inter alia, methods of treating age related diseases and methods for maintaining or improving the health of organs or body tissues and in particular for the treatment of diseases associated with a lack of compliance and or elasticity of vessels in particular airway and/or blood vessels.

BACKGROUND

As part of the ageing process there is a multi-system loss of cellular function, there is loss of elasticity of amongst other organs, the lungs and arterial vessels. In addition there is development of atheromatous plaques affecting the internal lumen of the arteries.

Chronic obstructive pulmonary disease (COPD) is also known as chronic obstructive lung disease (COLD), chronic obstructive airway disease (COAD), chronic airflow limitation (CAL) and chronic obstructive respiratory disease. It is a poorly reversible condition which usually gets progressively worse over time and refers to chronic bronchitis and emphysema, a pair of two commonly co-existing diseases of the lungs in which the airways become narrowed. This leads to a limitation of the flow of air to and from the lungs causing shortness of breath. The diagnosis of COPD requires lung function tests. Important management strategies are smoking cessation, vaccinations, rehabilitation, and drug therapy (often using inhalers). Some patients go on to requiring long-term oxygen therapy or lung transplantation. Worldwide, COPD ranked sixth as the cause of death in 1990 and the economic burden of COPD in the U.S. in 2007 was $42.6 billion in health care costs and lost productivity.

Impaired arterial blood flow is usually the result of atheromatous plaques and severe arterial occlusions are generally treated surgically whilst milder occlusions are treated by drug therapy (typically a combination of aspirin and 62-blockers) along with life style changes. Atheromatous plaques ultimately reduces the blood flow through the affected artery which ultimately leads to the destruction of the supplied organ due to ischemia. If this occurs in the brain there is a stroke, in the heart, myocardial infarction, in the legs intermittent claudication. At present medication may slow the rate of development of the plaque but it does not fully reverse the presence of the atheromatous plaque and to date there is no treatment that affects or restores the elasticity of the arteries. Impaired arterial blood flow causes a number of conditions depending on which organ or tissue is deprived of a normal oxygen rich blood supply. For example, angina pectoris is chest pain caused by myocardial ischemia, an inadequate supply of blood-borne oxygen to the heart muscle. Patients with stable angina experience pain after exercise or stress, which disappears when they rest. However, if the arterial impairment is in penile arterial flow then the individual may suffer from erectile dysfunction similarly if the flow is restricted in limbs the individual may suffer intermittent claudication or cramping, if the impairment is in renal arterial flow a function then the individual may suffer a decline in renal function which in some cases results in renal failure. If the impaired arterial flow causes transient ischaemic attacks then the brain may be affected.

A cost effective non-invasive treatment that could improve compliance and or elasticity of vessels in particular airway and/or blood vessels and so improve fluid flow in narrowed vessels would offer immediate benefit to sufferers and clinicians alike.

It is known from the prior art that electromagnetic radiation centred at around 1072 nm is particularly effective at treating herpetic and bacterial infections (WO9919024) and that this particular wavelength also can be used cosmetically to ameliorate the appearance of superficial skin fine lines and wrinkles (WO 2006/000757). However, in the present invention it has been found surprisingly that electromagnetic radiation can also be effective in treating other conditions the symptoms and causes of which lie not on the skin surface but deep beneath the surface of the skin.

BRIEF SUMMARY OF THE DISCLOSURE

According to the present invention there is provided an apparatus that sized and shaped so as to enclose at least a chest/thoracic region or the whole of a human or animal body, so that in use the individual will receive during treatment a substantially 360° exposure to therapeutic light, the apparatus comprising an outer surface and an inner surface which is to be in contact with or in close proximity to the part to be treated, the inner surface comprising means for emitting divergent electromagnetic radiation centred around 1072 nm and being capable of producing, at the site being treated, a radiation intensity of at least 20 mW/cm$^2$ and up to 5 W/cm$^2$.

Reference herein to a site being treated is intended to include, without limitation, the bones, vessels or internal organ of a human or animal subject.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The "outer surface" of the apparatus is the surface which is not in contact or close proximity to the individual being treated and is the exterior wall of the apparatus. The "inner surface" is the treatment surface and comprises the means for emitting electromagnetic radiation and as such is the surface that, in use, will be closest to the area of the individual to be treated.

In one embodiment of the invention the apparatus comprises a plurality of hinged panels which may be folded about the individual to be treated. During treatment, the individual may be erect or supine to receive the electromagnetic radiation and as such the area to be treated can be encased in the apparatus. The panels themselves may be constructed of a rigid material or a relatively flexible material.

In another embodiment of the invention the apparatus comprises a substantially "C" shaped device wherein, in use, a limb or trunk of the individual can be placed within the hollow lumen of the device. Preferably the "C" shaped device is made of a relatively flexible material so that it may be partially expanded so that it can be fitted about the individual.

In a yet further embodiment of the invention the apparatus comprises a front and back panel the front and/or back panel (s) being contoured or profiled to fit about the chest or torso of an individual. It is conveniently referred to as the "chest apparatus". The panels are shaped so as to allow spaces or gaps for the head, arms and lower torso to protrude so that when worn and in place, the individual appears to be wearing a chest plate similar to that part of a suit of armour.

Preferably, the front and back panels are fastened together about the individual by any suitable means such as a snap fit mechanism or clip, the securing means are arranged at the periphery of each panel so that the individual may be securely encased in the apparatus.

Preferably, the inner surface of the front panel comprises a plurality of means for emitting electromagnetic radiation and optionally the back panel may also be provided with means for emitting electromagnetic radiation so that the individual will receive during treatment a substantially 360° exposure to 1072 nm.

Preferably, the means for emitting electromagnetic radiation on the inner or treatment surface of the front panel are arranged so that in particular areas there is a greater number of the means so that particular selected areas of the individual, such as the apex of lungs, will receive a greater concentration of light therapy. In the instance where the back panel is also provided with means for emitting electromagnetic radiation, these too may also be arranged so as to provide a greater concentration of light therapy at selected areas of the individual.

Preferably, the chest apparatus further includes curved shoulder applicators. The curved shoulder applicators may be in the front or back panel or may be positioned in each panel so that when in use the complementary panels will form the curve for the individual's shoulder.

Preferably, the front panel also includes a projecting portion for directing light to the inferior aspect of the myocardium.

Preferably, at least some the means for emitting electromagnetic radiation on the inner surface of the front panel are angled or so as to ensure maximum penetration between rib spaces of the individual.

In the instance where the back panel is also provided with means for emitting electromagnetic radiation, these too many be arranged and angled to provide maximum therapy and penetration.

In a yet further embodiment of the apparatus of the present invention, the apparatus comprises a front and back panel which are sized and shaped so as to encase substantially the whole body of an individual to be treated. This embodiment is conveniently referred to as the "whole body" device. In this embodiment of the invention the apparatus comprises a front and back panel which is the shape of an individual in a star form, that is to say that the arms are outstretched to the side and the legs are an inverted "V". This embodiment of the invention is particularly effective for providing simultaneous treatment to a wide variety of body parts and tissues and has been shown to provide a particularly effective therapy. The apparatus comprises complementary front and back panels which are symmetrical about a central horizontal plane and are sized and shaped so as to encase the whole body of an individual to be treated, the front and back panel comprise a head region for accommodating an individual's head, a body region of accommodating an individual's torso and pelvic region, a pair of arm regions for accommodating an individual's arms held away from between an angle of 20-90° from the body and a pair of leg regions for accommodating an individual's legs in an inverted "V" position.

Preferably, the front and back panels of the whole body apparatus are fastened together about the individual by any suitable means such as a snap fit mechanism or clip, the securing means are arranged at the periphery of each panel so that the whole body of the individual may be securely encased in the apparatus. The individual may be erect or supine to receive the treatment.

Preferably, the inner surface of the front panel comprises a plurality of means for emitting electromagnetic radiation and optionally the back panel may also be provided with means for emitting electromagnetic radiation so that the individual will receive during treatment a substantially 360° exposure to 1072 nm.

Preferably, the means for emitting electromagnetic radiation on the inner or treatment surface of the front panel are arranged so that in particular areas there is a greater number of the means so that particular selected areas of the individual, such as the pelvic region and organs such as the uterus, prostate or bladder, will receive a greater concentration of light therapy. In the instance where the back panel is also provided with means for emitting electromagnetic radiation, these too may also be arranged so as to provide a greater concentration of light therapy at selected areas of the individual. In this way the individual receives a whole body 360° exposure to 1072 nm.

Preferably, at least some the means for emitting electromagnetic radiation on the inner surface of the front and/or back panels are angled or so as to ensure maximum penetration.

By divergent it meant that the electromagnetic radiation emitted from the system of the invention has a divergent half angle of at least 5°. Preferably divergence of the electromagnetic radiation is in the range 15° to 45° half angled divergent.

Preferably, the electromagnetic radiation centred around 1072 nm has a bandwidth of about 5 to 120 nm, and more preferably still the bandwidth is less than 50 nm and around 10 nm. It is desirable that the operating peak output of the wavelength of the light emitting devices be within 0 to 10 nm and more preferably 2-5 nm of 1072 nm. Studies have shown that the wavelength centred around 1072 nm is particularly effective at treating bones, joints, kidneys, liver, vessels and lung tissue.

The radiation producing means are preferably solid state light emitting devices, more preferably solid state light emitting diodes, gas discharge devices or light emitting polymers. The radiation from such devices can be electrically operated or the radiation can be delivered to an applicator via a fibre-optic delivery system.

Preferably, the radiation emitter includes a PN junction arranged to emit radiation with a wavelength centering at or about 1072 nm. A single light diode assembly may include a plurality of orientated junctions. Infrared emitting diodes may be arranged not only to emit radiation at a specific frequency but also to emit a high intensity divergent beam. A gas discharge device may include a mixture of gases which will give an output at the desired wavelength, for instance, 1072 nm. The desired wavelength of light may also be produced by a light emitting polymer.

Another preferred radiation producing means is a laser diode device, an example being a laser diode emitting light at a frequency of 1072 nm. Such a light emitting means is of low power intensity having a divergent beam and not giving rise to thermal damage. It may be used to treat many conditions, including emphysema (COPD) and atherosclerotic plaques.

In a particularly preferred embodiment of the invention, the means for emitting divergent electromagnetic radiation is a light emitting diode (LED). The radiation emitter includes a PN junction arranged to emit 1072 nm light, a single LED may include a plurality of orientated junctions. The apparatus of the present invention includes a plurality of LEDs arranged on a surface of the apparatus which is to be in contact with or in close proximity to the site being treated of the human or animal body.

Preferably, the space between the means for emitting electromagnetic radiation is between 2 to 25 mm apart, more preferably they are between 3 to 15 mm apart and more preferably still are between 3 to 10 mm apart. It will be appreciated that the inner surfaces of the apparatuses of the present invention may comprise a variety of spacings between the multiple LEDs or similar devices so that in some areas where treatment is most required and the intensity level needs to be high, the LEDs will be closer together compared to areas not requiring a high level of treatment and where the intensity requirement is less.

Preferably, the 1072 nm light has uniform light distribution.

Preferably, the apparatus is associated with a power supply such as mains electricity or it may be battery powered.

Preferably the electromagnetic radiation is continuous or pulsed.

Preferably when the electromagnetic radiation is continuous the intensity is at least 20 mW/cm$^2$ for treatment of superficial bones and up to 5 W/cm$^2$ for the treatment of deeper organs such as the heart, lungs and vessels of the brain.

Preferably when the electromagnetic radiation is pulsed the intensity is at least 500 mW/cm$^2$ peak power for treatment of superficial joints such as knees and preferably is at least 2 W/cm peak power for treatment of Lungs and heart and the average power is up to 4 W/cm$^2$. The average power is the peak power multiplied by the proportion of the total time that the radiation is applied. For instance if the peak power is 500 mW/cm$^2$ and is pulsed for 200 microseconds at a frequency of 600 Hz then the average power is 30 mW/cm$^2$.

Preferably when the electromagnetic radiation is pulsed the average power of the intensity is in the region of 0.5-4 W/cm$^2$.

We have found that the power may suitably range from 500 mW/cm$^2$ peak to 4 W/cm$^2$ continuous or peak power when applied to the bones.

Preferably when the electromagnetic radiation is pulsed it is applied for pulse duration periods of at least 10-15 microseconds and more preferably is applied at a frequency/repetition rate in the range 200-900 Hz. More preferably still, the frequency/repetition rate is at, or about, 600 Hz.

Our studies have shown that the electromagnetic radiation can be either coherent or non-coherent the clinical outcomes are not affected by this parameter.

Preferably the electromagnetic radiation is applied to the affected area for at least 30 seconds and up to a few minutes. A typical exposure time for the bone and lungs is in the region of 6 minutes, however for tissues well below the skin surface this time is increased according to the individuals fat/muscle layer depth and exposure could be up to 10 minutes.

It should be appreciated that the power source emitting the electromagnetic radiation will have to produce more than the required intensity for the clinical effect since we have shown that approximately 95% of the applied therapeutic amount of light is lost across the skin surface during treatment. Thus the intensity of applied radiation will have to be corrected for when carrying out a treatment.

From the foregoing it is understood that the electromagnetic radiation may be directed to the target site either continuously or in a switched (pulsed) manner. The main benefit of switching enables power conservation and facilitates much higher peak power output, thereby improving clinical response.

Preferably the system further includes means for fixing the intensity of the radiation within a pre-determined range. The radiation output may be monitored with a visible display indicating correct function of the device both for intensity and wavelength.

Preferably the system further includes means for controlling the duration of the application of the radiation. Accordingly, the present invention is concerned with the use of electromagnetic radiation having a wavelength centred around 1072 nm and applied at a low intensity such that no thermal damage is caused to any human or animal tissues. The present invention does not rely upon thermal effects to achieve a therapeutic effect.

In the case where the system is to be used in such a way that radiation be caused to enter the eye, it is preferred that the power intensity does not exceed 100 mW/cm$^2$. Otherwise, the power intensity may be higher and can suitably be delivered in pulsed form, thereby obtaining several W of momentary power output, allowing good penetration of tissue and substantial systemic effect.

The present invention also provides the use of divergent electromagnetic radiation having a wavelength of 1072 nm and an intensity of at least 500 mW/cm$^2$ and up to 4 W/cm$^2$ to treat an area of biological tissue of a living human or animal subject.

Preferably the electromagnetic radiation as produced by the apparatus of the invention provides for treating conditions such as, without limitation, improvement of the elasticity in lungs in patients with chronic obstructive pulmonary disease and in treating atherosclerotic plaques. The use of restricted bandwidth radiation can enhance cellular production of elastin and increase cartilage production.

Preferably, apparatus of the present invention is capable of penetrating deep below the surface of the superficial skin from about 5 mm to 500 mm. The unexpected results from light treatment presented hereinafter confirm that light at 1072 nm does indeed have a beneficial therapeutic effect on organs and physiological processes deep below the skin surface.

According to a second aspect of the invention there is provided use of the apparatus of the first aspect of the invention for the treatment of diseases associated with a lack of compliance and/or elasticity of airway and/or blood vessels.

Preferably the disease is selected from the group comprising chronic obstructive pulmonary disease, atherosclerotic disease, ischaemic heart failure, cardiac insufficiency, angina pectoris and renal failure.

According to a third aspect of the invention there is provided use of divergent electromagnetic radiation centred around 1072 nm that produces, at the site being treated, a radiation intensity of at least 20 mW/cm$^2$ and up to 5 W/cm$^2$ for the treatment of diseases associated with a lack of compliance and/or elasticity of airway and/or blood vessels.

According to a fourth aspect of the invention there is provided a method of treating diseases associated with a lack of compliance and/or elasticity of airway and/or blood vessels, the method comprising treating an area of biological tissue of a living human or animal subject by applying to said area divergent electromagnetic radiation having a wavelength centred around 1072 nm having an intensity at the site to be treated of at least 500 mW/cm$^2$ and up to 4 W/cm$^2$.

Preferably, the area to be treated is irradiated so that the affected tissue receives at least 500-2000 mW/cm$^2$ peak power of radiant energy, depending on the tissue to be treated. A factor here is the period of irradiation and, preferably, the period should be at least a specified minimum of 10-15 microseconds at a repetition rate/frequency of 200-900 Hz and preferably for at least 30 seconds duration.

The treatments can be repeated as often as is necessary in order to observe an improvement in the condition that is being treated.

Preferably, the disease is selected from the group comprising chronic obstructive pulmonary disease, atherosclerotic disease, ischaemic heart failure, cardiac insufficiency, angina pectoris and renal failure.

According to a fifth aspect of the invention there is provided a method of treating chronic obstructive pulmonary disease, the method comprising:
(i) exposing at least the thoracic/chest region of an individual suffering from the disease to divergent electromagnetic radiation having a wavelength centred around 1072 nm and having an intensity at the site to be treated of at least 500 mW/cm$^2$ and up to 4 W/cm$^2$ for at least 10-15 microseconds at a repetition rate/frequency of 200-900 Hz;
(ii) maintaining the exposure for at least 30 seconds; and
(iii) repeating the exposure as frequently as required.

According to a sixth aspect of the invention there is provided a method of treating cardiac circulatory disorders, the method comprising:
(i) exposing at least the thoracic/chest region of an individual suffering from the disease to divergent electromagnetic radiation having a wavelength centred around 1072 nm and having an intensity at the site to be treated of at least 500 mW/cm$^2$ and up to 4 W/cm$^2$ for at least 10-15 microseconds at a repetition rate/frequency of 200-900 Hz;
(ii) maintaining the exposure for at least 30 seconds; and
(iii) repeating the exposure as frequently as required.

It will be appreciated that preferred features ascribed to one particular aspect of the invention are to be applied mutatis mutandis to each and every aspect of the invention.

BRIEF DESCRIPTION OF THE DRAWINGS

Embodiments of the invention are further described hereinafter with reference to the accompanying drawings, in which:

FIGS. 4A to 4E shows an alternative embodiment of the apparatus of the present invention wherein the apparatus is configured so as to encase the thoracic or chest region of an individual.

DETAILED DESCRIPTION

Figure 1:
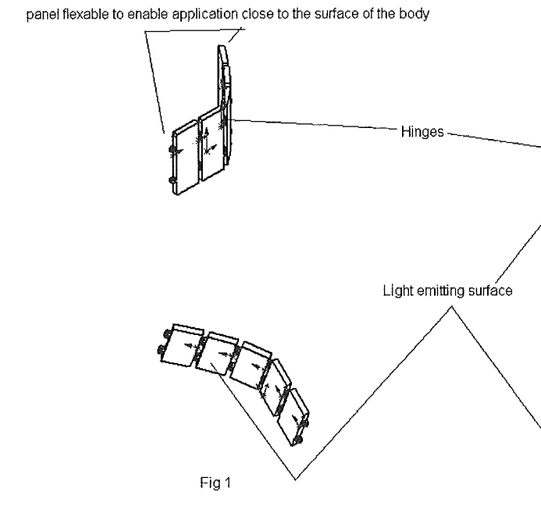
FIGS. 1 and 2 show one particular embodiment of the apparatus of the present invention wherein the apparatus comprises a series of hinged panels each having a plurality of light emitting devices on the surface which is in contact with or in close proximity to a part of the human or animal body to be treated.
Figure 2:
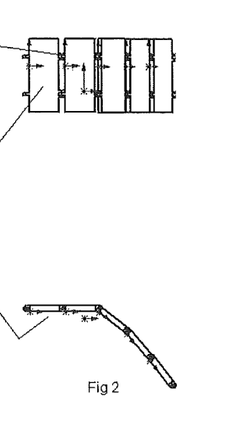

In one embodiment of the invention the apparatus for emitting electromagnetic radiation comprises a series of hinged panels (FIGS. 1 and 2) each panel comprising a light emitting surface and a non-emitting surface. The light emitting surface is the surface that is in contact with or in close proximity to the surface of the animal or human body which is to be treated. The light emitting surface comprises a plurality of that LEDs arranged so that uniform light distribution is achieved over the affected area. The LEDs may be embedded in the panel or fixedly attached thereto. Panels are hinged at upper and lower edges with an adjacent panel so that the panels are flexible and can be wrapped around a body or body part. The hinges may be releasable detachable so that the series can be two or more panels depending on a users requirements. The panels can vary in size so as to enable large areas of the human body to be treated.

Figure 3:
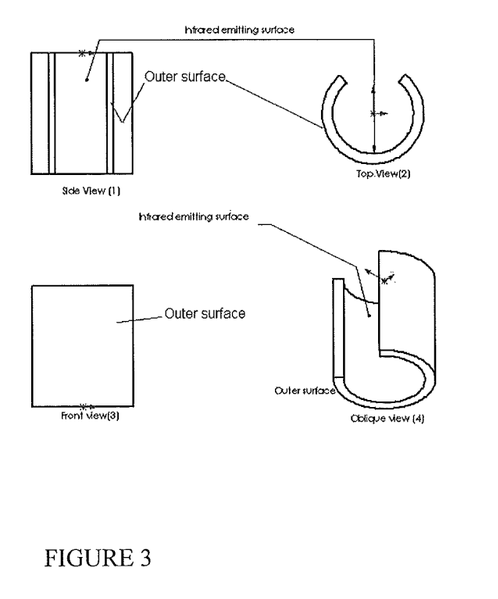
FIG. 3 shows a rigid version of the apparatus of the present invention wherein the electromagnetic radiation is directed in a semi-circular fashion towards an appendage placed within the substantially "C" shaped apparatus.
Figure 4A:
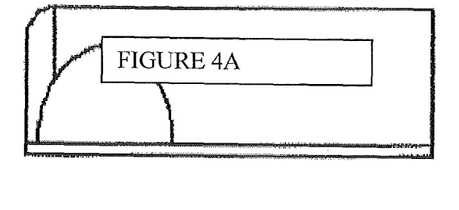
FIG. 4A shows a side view.
Figure 4B:
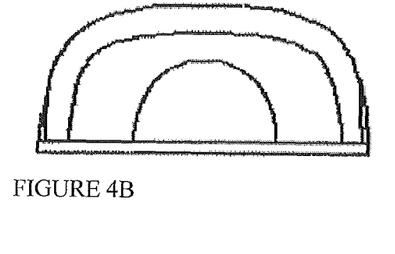
FIG. 4B shows a head end view.
Figure 4C:
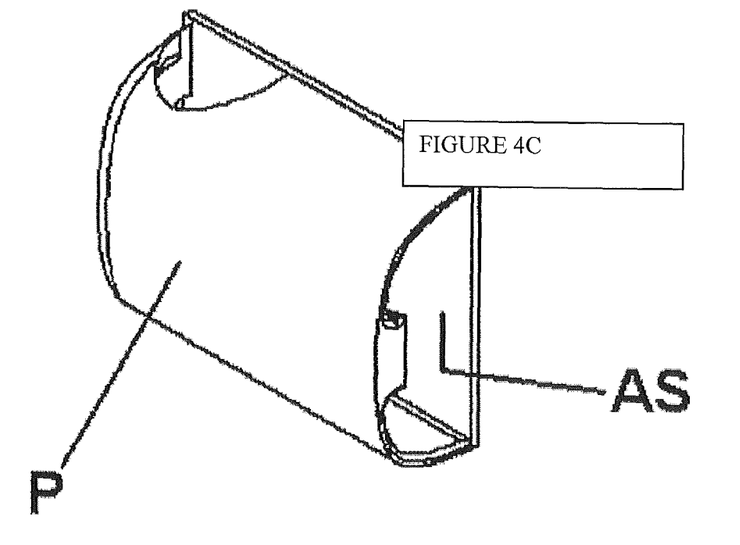
FIG. 4C shows a leg end view.
Figure 4D:
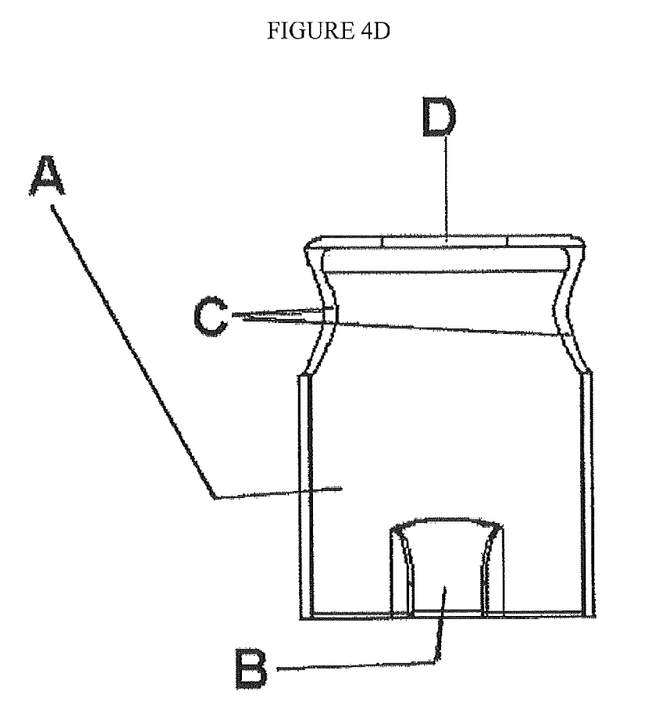
FIG. 4D shows an internal view of the upper or chest encasing part of the apparatus and FIG. 4E shows a side view of FIG. 4D.
Figure 4E:
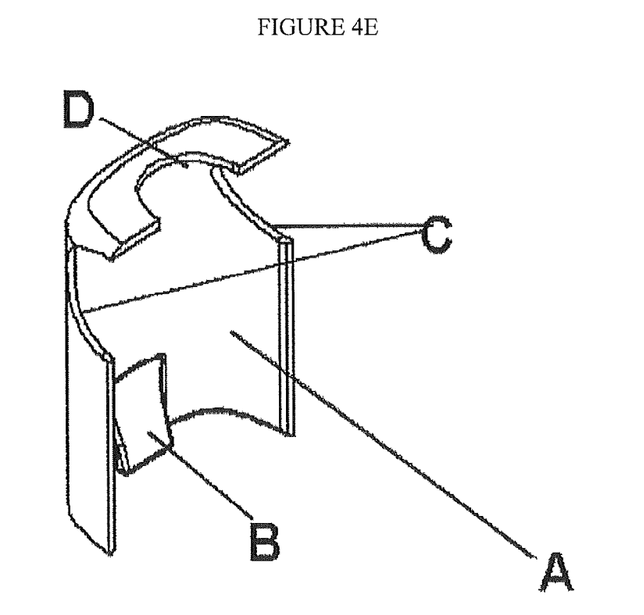

In an alternative embodiment of the invention as depicted in FIG. 3, the apparatus comprises a substantially "C" shaped open ended device wherein the inner surface is provided with a plurality of LEDs embedded therein or attached thereto and arranged so that uniform light distribution is achieved over the affected area. The "C" shaped devise is sufficiently flexible to allow an individual to expand it so as to enter into the lumen and have it placed about the chest region. The device may be secured about the individual by straps or the like. This particular embodiment of the invention is particularly well suited to irradiation of arms, legs, trunk and chest depending on the size of the "C" shaped device.

FIG. 4 shows an alternative embodiment of the invention for irradiating the chest region. The main function of this light applicator is to facilitate the simultaneous treatment of all the aspects of the chest from all directions. In the event the light is pulsed, the "ON" pulses all coincide, hence achieving a greater penetration of the target tissue.

There are aspects of the design which are superior over the stand light panel approach, the curved shoulder light applicators D will treat the apex of the lung tissue which is often the site of significant pulmonary pathology. The prominence B, directs light to the inferior aspect of the myocardium, which would otherwise not be irradiated. The minimal local pressure in the epigastric region will increase light transmission to the target area by compressing the anterior abdominal fat and displacing the upper abdominal contents inferiorly and laterally. Light emitting surface A, has the light sources structured so as to angle slightly superiorly to ensure maximal penetration between the rib spaces. In use, arms are placed through C, and folded across the outside of the light emitting apparatus onto the external surface P, by doing this the scapulae are rotated laterally and allow the light from the posterior surface AS to irradiate the posterior aspect of the chest.

Figure 5A:
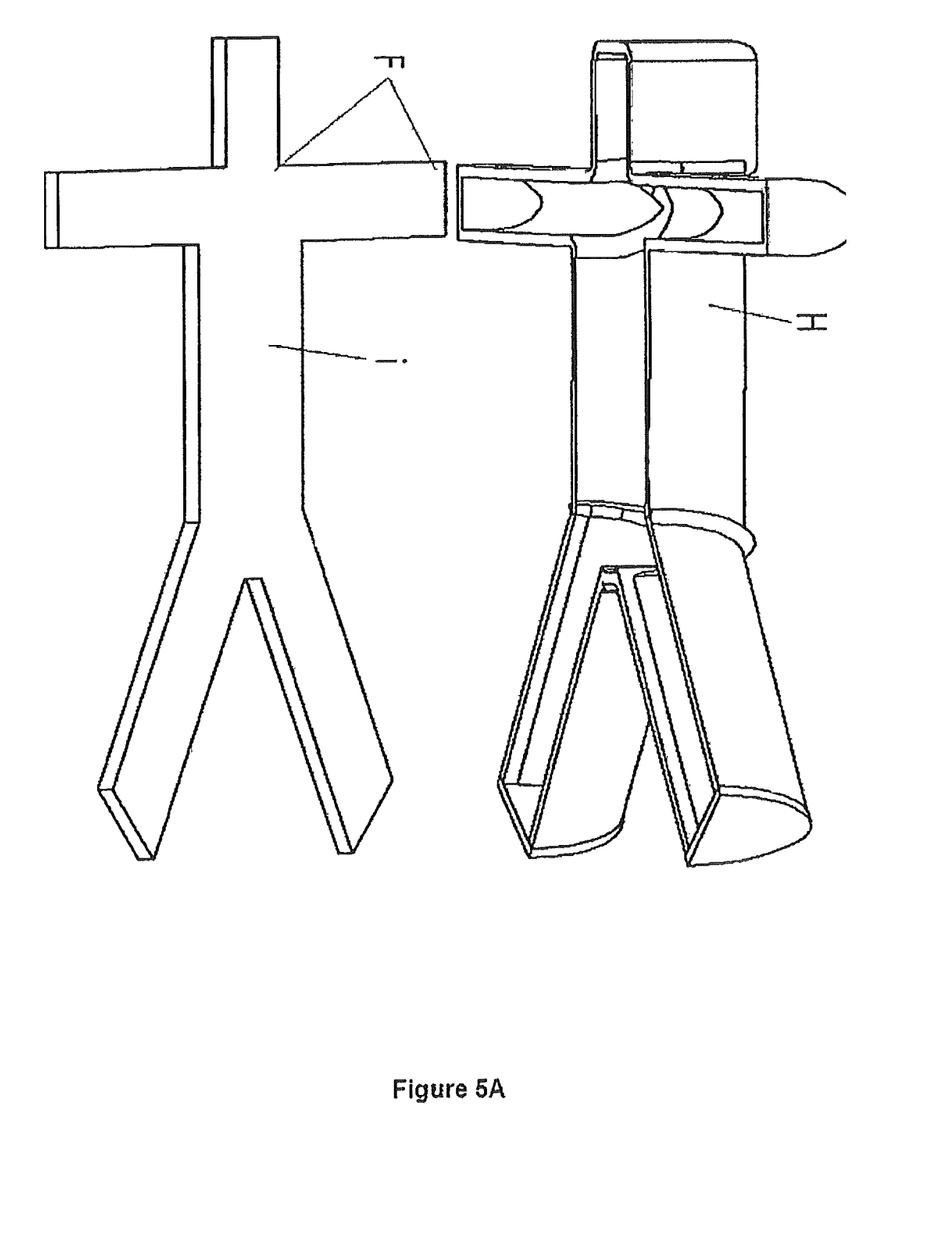
FIG. 5A shows a further alternative of the apparatus of the present invention for use in whole body electromagnetic radiation with the rear and front portions in disassembled form.
Figure 5B:
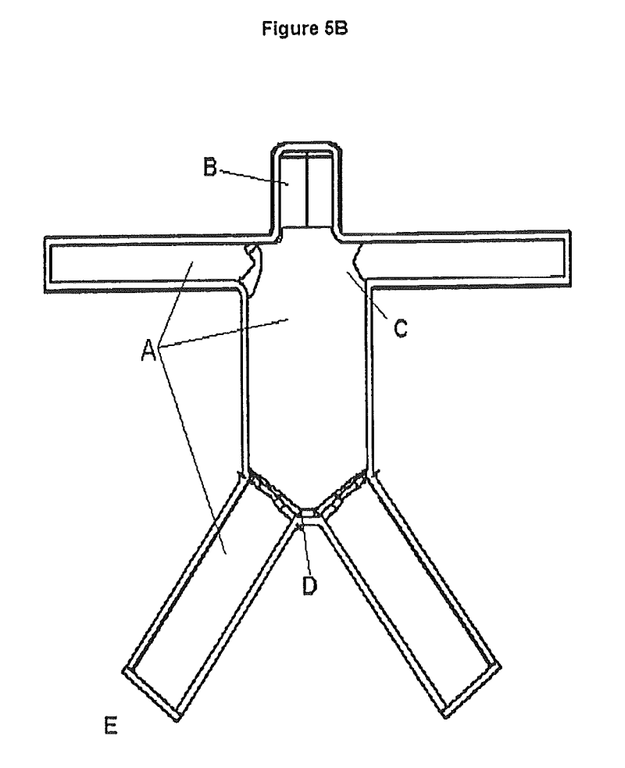
FIG. 5B shows the internal surface of the front portion that encases the front of the body as seen in FIG. 5A.

FIGS. 5A and 5B show a whole body irradiation apparatus. It has been found that traditional panels such as those placed around the body and used in a sun bed will not achieve the desired objective as the limbs will obstruct the light which results in a suboptimal therapeutic effect. It has been found that simultaneous irradiation by 1072 nm of the whole body delivers a superior result. Notably bone provides a significant impediment to 1072 nm light, thus by raising the arms, there is a reduction in the volume of tissue between the light emitting surface C (FIG. 5B) and the thoracic cavity is reduced allowing greater penetration of light to deeper structures such as the heart and mediastinum. Moreover, as blood is being actively transported around the body, the only way to ensure that all the cells in the blood are being treated for the required treatment time is to irradiate the entire body simultaneously. The device in FIGS. 5A and 5B can either be custom made for an individual or manufactured in set sizes to fit the majority of the population.

It has been found that the treatment of the pelvis provides a difficult scenario as the density of the bone in this region is high. With reference to FIG. 5A, high density light sources at D irradiate the peritoneal region and hence treat the pelvic organs such as uterus or prostate and bladder. Surfaces A and B are light emitting surfaces which irradiate the entire surface of the human body. Surface E is a light emitting source which will treat the plantar aspect of the foot.

In use, an individual lies or stands against the light emitting source F which is provided with a plurality of LEDs arranged to emit uniform distribution of light from light emitting surface "i". The individual's arms and legs are placed in a position so as to be in contact with the shape of F. The body contouring light source H is placed over the patient for the desired treatment duration. In effect the patient is encapsulated in a light emitting body profiled capsule wherein light is emitted from both front and back panels so as to provide substantially 360° of irradiation. Optionally, the device is provided with a means to circulate air so that the individual does not become overheated.

Examples of the invention will now be described with reference to the treatment of particular conditions.

EXAMPLE 1

Angina is the term applied the pain that occurs when the oxygen supply of the heart is outstripped by the heart's activity. This is generally associated with a reduction in blood flow to the heart as a result of narrowed coronary vessels which in turn is often caused by atheromatous plaque. Exercise tolerance of patients with angina is often predictable and measurable, going up an incline is more likely to precipitate an angina attack than going down an incline due to the increased oxygen demand of the muscle of the body and hence the increase rate and strength the heart needs to pump and hence increasing the oxygen and blood flow requirement of the heart.

Treating 10 patients with exercise induced stable angina with the 1072 nm chest device (as depicted in FIGS. 4A-E) resulted in 2 patients being able to walk briskly up a flight of stairs without experiencing any angina pain, for these 2 individuals they consistently needed to rest half way up a single storey flight of stairs. This achievement was after 2 months of 6 minute, 5 times a week treatment.

6 participants, improved their exercise tolerance by 25%, being able to walk an average of 200 meters on a flat surface without experiencing angina, their previous average effort tolerance was below 150 meters for the same period of time. This was achieved with 4-5 treatments of 6 minutes a day weekly. The remaining 2 participants demonstrated a moderate improvement of effort tolerance of 15%, with only three 6 minute treatments of the 1072 nm light on consecutive days weekly.

Given that the monitoring period was only for a 2 month period, it is anticipated that the improvement will continue beyond this period and therapeutic efficacy will be improved over a longer period of use.

In another set of patients, light emitting panels were placed against the abdomen and the renal angles so as to treat the renal arteries. A total of 5 patients has reduced renal blood flow due to atheroma. After 8 weeks of daily treatment renal blood flow had increased.

EXAMPLE 2

In COPD there has been destruction of normal lung tissue which has been replaced with scar tissue. Normal lung tissue has a high degree of elasticity which allows the lungs to contract to a small fraction of their volume if it were not for the vacuum between the chest wall and the lungs in the pleural cavity. Loss of this elasticity results in reduced lung compliance and poorer lung function in addition to the destruction of the alveolar lung tissue itself. Improving the elasticity of the lungs will facilitate a greater movement of air in and out of the lungs with each breath, which in itself will result in improved oxygenation of the blood.

20 participants were treated with 1072 nm by the chest device (as depicted in FIGS. 4A-E), measurements were related to lung function and to effort tolerance before breathlessness forced the participants to rest. All participants had a once daily treatment of 6 minutes 5 days a week with the 1072 nm chest treatment device for a 2 month period. 10 of the patients had an effort tolerance of 75 meters in 2 minute, which then was followed by a rest period. After a 2 month treatment with the chest 1072 nm treatment device, 6 minutes a day, 5 days a week, this was increased from 75 meters to 100 meters. Lung function tests in the 10 participant: Results showed that the Forced Vital Capacity (FVC)—post treatment increased by 10% on average and that, Forced Expiratory Volume in 1 second (FEV1)—post treatment improved by 15% on average. 5 individuals had an effort tolerance of 150 meters on a flat surface in 3 minutes, this improved to 180 meters in 3 minutes after treatment. Results showed that FVC—improved by 12% on average post treatment and that FEV1—improved by 14% post treatment on average. The final 5 individuals became breathless with mild to moderate activity of walking up a flight of stairs. After the 2 months treatment of the 1072 nm chest device, the degree of breathlessness was decreased which was reflected in the lung function tests. Results showed that FVC—improved on base line by 15% after 2 months of 1072 nm treatment and that FEV1— improved on base line by 20% on average after 2 months of 1072 nm treatment.

EXAMPLE 3

Other conditions were investigated, 5 patient with established physical disability due to ischaemia from a vascular occlusion were exposed to 1072 nm and all a marked improvement of their physical disability 3 weeks after daily treatment. In addition, 5 patients with established physical disability due to ischaemia from a vascular occlusion were treated again all 5 patients had a marked improvement of their physical disability 3 weeks after daily treatment with 1072 nm light. In a yet further patient group 10 patients with established heart failure were treated with 1072 nm light, all 10 showed improvement in their breathlessness and left ventricular ejection systolic fraction. Other results, using the whole body device as depicted in FIGS. 5A and 5B, showed that when treating more than 40% of the body surface area with 1072 nm light there is an improvement in body function, making the person more energetic and capable of physical activity, a general improvement in physiological function and appearance was also observed.

The invention claimed is:

1. A method of treating chronic obstructive pulmonary diseases associated with a lack of compliance and/or elasticity of an airway within a body cavity, the method comprising treating a superficial area of skin of a chest/thorax abdomen or a whole body of a living human or animal subject by applying to said area divergent electromagnetic radiation having a wavelength centered around 1072 nm having an intensity of at least 500 mW/cm^2 and up to 4 W/cm^2 at the site to be treated, wherein the method is non-invasive, and wherein the radiation penetrates below the superficial area of skin from about 5 mm to 500 mm to tissues and organs within the body cavity and wherein the method does not rely on thermal effects to achieve a therapeutic effect.

2. A method according to claim 1 wherein the superficial area of skin to be treated is irradiated so that the affected tissue within the body cavity receives at least 500-2000 $mW/cm^2$ peak intensity of radiant energy for at least a minimum of 10-15 microseconds at a repetition rate/frequency of 200-900 Hz and wherein a treatment duration is for at least 30 seconds.

3. A method according to claim 1 wherein divergence of the electromagnetic radiation is in the range 15° to 45° half angled divergent.

4. A method according to claim 1 wherein the electromagnetic radiation centred around 1072 nm has a bandwidth of between 5 to 120 nm.

5. A method according to claim 1 wherein an operating peak output of an electromagnetic radiation source is within 0 to 10 nm of 1072 nm.

6. A method according to claim 1 wherein the electromagnetic radiation is emitted from at least one of solid state light emitting devices, laser diode, solid state light emitting diodes, gas discharge devices and/or light emitting polymers.

7. A method according to claim 1 wherein the electromagnetic radiation centred around 1072 nm has uniform light distribution.

8. A method according to claim 1 wherein the electromagnetic radiation is continuous or pulsed.

9. A method according to claim 1 wherein when the electromagnetic radiation is pulsed, an intensity of the electromagnetic radiation is at least between 500 $mW/cm^2$ and 2 $W/cm^2$ peak power and wherein an average intensity is up to 4 $W/cm^2$.

10. A method according to claim 1 wherein a treatment area is selected to treat a disease within a body cavity selected from the group consisting of chronic bronchitis and emphysema.

11. A method according to claim 1, wherein the method is non-invasive.

* * * * *

UNITED STATES PATENT AND TRADEMARK OFFICE
CERTIFICATE OF CORRECTION

PATENT NO. : 9,079,021 B2  Page 1 of 1
APPLICATION NO. : 13/003958
DATED : July 14, 2015
INVENTOR(S) : Gordon Dougal It is certified that error appears in the above-identified patent and that said Letters Patent is hereby corrected as shown below:

In the Specification:
Column 1, Line 54: Please correct "and 62-blockers)"
to read -- and β-blockers) --

Signed and Sealed this
Thirty-first Day of May, 2016

Michelle K. Lee
*Director of the United States Patent and Trademark Office*